United States Patent
Lee et al.

(10) Patent No.: US 11,272,851 B2
(45) Date of Patent: Mar. 15, 2022

(54) PULSE SENSING MODULE, BLOOD PRESSURE CALCULATION MODULE, BLOOD PRESSURE MEASURING DEVICE AND METHOD FOR MANUFACTURING PULSE SENSING MODULE

(71) Applicants: ROBOPRINT CO., LTD, Gyeongsan-si (KR); KOREA ADVANCED INSTITUTE OF SCIENCE AND TECHNOLOGY, Daejeon (KR)

(72) Inventors: Keon Jae Lee, Daejeon (KR); Dae Yong Park, Daejeon (KR); Dong Hyun Kim, Daejeon (KR); Seong Wook Min, Daejeon (KR); Jae Hun An, Daejeon (KR); Jung Kyu Park, Daegu (KR); Min Su Kim, Gyeongju-si (KR)

(73) Assignees: ROBOPRINT CO., LTD, Gyeongsan-si (KR); KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 510 days.

(21) Appl. No.: 16/202,965

(22) Filed: Nov. 28, 2018

(65) Prior Publication Data
US 2020/0155010 A1 May 21, 2020

(30) Foreign Application Priority Data

Nov. 16, 2018 (KR) .......... 10-2018-0141347
Nov. 16, 2018 (KR) .......... 10-2018-0141348
Nov. 16, 2018 (KR) .......... 10-2018-0141349

(51) Int. Cl.
A61B 5/022 (2006.01)
A61B 5/00 (2006.01)
A61B 5/021 (2006.01)

(52) U.S. Cl.
CPC .......... *A61B 5/022* (2013.01); *A61B 5/02108* (2013.01); *A61B 5/6824* (2013.01); *A61B 5/02141* (2013.01); *A61B 2560/0214* (2013.01)

(58) Field of Classification Search
CPC ............ A61B 5/021–022; A61B 5/024; A61B 5/02108
See application file for complete search history.

(56) References Cited

U.S. PATENT DOCUMENTS 5,551,437 A * 9/1996 Lotscher ................ A61B 5/025 600/485
2006/0195035 A1* 8/2006 Sun ..................... A61B 5/02116 600/503

(Continued)

FOREIGN PATENT DOCUMENTS

JP   H07503648 A   4/1995
KR   10-1059528 B1  8/2011

(Continued)

*Primary Examiner* — Daniel L Cerioni
*Assistant Examiner* — Raymond P Dulman
(74) *Attorney, Agent, or Firm* — Maschoff Brennan

(57) ABSTRACT

A pulse sensing module used in a blood pressure measuring device attached to the skin to allow at least one of systolic pressure $P_{systolic}$, diastolic pressure $P_{diastolic}$, and blood pressure variation to be measured according to an embodiment of the present disclosure includes a piezoelectric layer that includes a piezoelectric material for generating a piezoelectric effect due to a pulse and a protective layer that is applied to the piezoelectric layer to protect the piezoelectric layer, allows a poling process of applying a high voltage to the first electrode line and the second electrode line formed on the piezoelectric layer to improve the polarity of the piezoelec- (Continued)

tric material, and has an opening for allowing a portion of the first electrode line and a portion of the second electrode line to be exposed.

12 Claims, 19 Drawing Sheets

(56) References Cited

U.S. PATENT DOCUMENTS

| | | | |
|---|---|---|---|
| 2010/0274143 A1* | 10/2010 | Kim | A61B 5/022 600/493 |
| 2012/0289839 A1 | 11/2012 | Takenoshita et al. | |
| 2013/0041244 A1* | 2/2013 | Woias | A61B 5/0215 600/381 |
| 2015/0305632 A1* | 10/2015 | Najarian | A61B 5/7207 600/301 |
| 2017/0086686 A1* | 3/2017 | Narasimhan | A61B 5/02444 |
| 2018/0206734 A1* | 7/2018 | Lin | A61B 5/02007 |
| 2019/0011288 A1* | 1/2019 | Nassar | A61B 5/445 |
| 2019/0189905 A1* | 6/2019 | Benedict | C08L 29/14 |
| 2019/0223736 A1* | 7/2019 | Wang | A61B 5/02108 |
| 2020/0054221 A1* | 2/2020 | Ward | A61B 5/0295 |
| 2020/0060558 A1* | 2/2020 | Aleksov | A61B 5/02141 |
| 2020/0305740 A1* | 10/2020 | Quan | A61B 5/6844 |
| 2020/0337569 A1* | 10/2020 | Tauban | C08J 5/18 |

FOREIGN PATENT DOCUMENTS

| | | |
|---|---|---|
| KR | 10-2013-0094858 A1 | 8/2013 |
| KR | 10-2017-0106099 A1 | 9/2017 |

* cited by examiner

PULSE SENSING MODULE, BLOOD PRESSURE CALCULATION MODULE, BLOOD PRESSURE MEASURING DEVICE AND METHOD FOR MANUFACTURING PULSE SENSING MODULE

CROSS-REFERENCE TO RELATED APPLICATION

This application claims priority to and the benefit of Korean Patent Application Nos. 2018-0141347, filed on Nov. 16, 2018, 2018-0141348, filed on Nov. 16, 2018, 2018-0141349, filed on Nov. 16, 2018 the disclosure of which is incorporated herein by reference in its entirety.

BACKGROUND

1. Field of the Invention

The present disclosure relates to a pulse sensing module, a blood pressure calculation module, a blood pressure measuring device, and a method of manufacturing a pulse sensing module, and more particularly, to a pulse sensing module, a blood pressure calculation module, a blood pressure measuring device, and a method of manufacturing a pulse sensing module, which measure blood pressure using a piezoelectric effect through a piezoelectric material.

2. Discussion of Related Art

Recently, living standards and health consciousness are rising such that interest and demand for health checkups are increasing.

In general, basic medical treatments for checkup are to measure blood pressure, pulse waves, electrocardiogram, and body fat, which are used as basic data.

To this end, each clinic is equipped with a blood pressure monitor for blood pressure measurement, an electrocardiogram measuring device for electrocardiogram measurement, a body fat measuring device for body fat measurement, a pressure pulse wave meter for pulse wave measurement, and a volume pulse meter for blood flow measurement.

Among the devices, the blood pressure monitor for blood pressure measurement has a method of tying a compression part having a tourniquet shape around an upper arm of a testee, tightening the compression part to fit the circumference of the upper arm, and measuring the blood pressure, as disclosed in Korean Patent Registration No. 10-1059528.

However, blood pressure measurement in such a manner causes inconvenience in that a testee needs to tighten a compression part having a tourniquet shape with one hand when measuring the blood pressure by himself or herself.

Further, a blood pressure measuring device has been recently used in which a space into which an upper arm of a testee is inserted is formed in a circular shape in a fixed manner and wherein, when the testee inserts the upper arm into the circular space and pushes a button, a compression part automatically swells to tighten the upper arm.

However, since such a blood pressure measuring device needs to allow an upper arm of a testee to be inserted into a circular space, a distance by which the testee's arm should be moved is increased, thereby causing user inconvenience. A testee who has difficulty in moving the elbow or shoulder needs to move the entire body rather than the joints and insert the arm, which leads to inconvenience in measurement.

Therefore, it is urgent to develop a blood pressure measuring device which measures blood pressure accurately by a simple method while minimizing the inconvenience of a testee in blood pressure measurement.

SUMMARY OF THE INVENTION

The present disclosure is directed to providing a pulse sensing module, a blood pressure calculation module, a blood pressure measuring device, and a method of manufacturing a pulse sensing module which clearly define a relationship between a voltage signal caused by a piezoelectric effect of a piezoelectric material and blood pressure while enabling blood pressure measurement through the piezoelectric effect on pulse so as to enhance accuracy of blood pressure measurement.

According to an embodiment of the present disclosure, there is provided a pulse sensing module used in a blood pressure measuring device attached to the skin to measure at least one of systolic pressure, diastolic pressure, and blood pressure variation, which includes: a piezoelectric layer that includes a piezoelectric material for generating a piezoelectric effect due to a pulse, wherein a first electrode line and a second electrode line disposed to be spaced apart from each other are formed on one surface of the piezoelectric layer; and a protective layer that is applied to the piezoelectric layer to protect the piezoelectric layer, allows a poling process of applying a high voltage to the first electrode line and the second electrode line to improve the polarity of the piezoelectric material, and has an opening for allowing a portion of the first electrode line and a portion of the second electrode line to be exposed such that the first electrode line and the second electrode line are electrically connected to a blood pressure calculation module of the blood pressure measuring device, wherein the blood pressure calculation module calculates the at least one of the systolic pressure, the diastolic pressure, and the blood pressure variation using a voltage signal generated by the piezoelectric effect.

The opening may include a first opening and a second opening that are formed in positions corresponding to those of an end portion of the first electrode line and an end portion of the second electrode line.

The protective layer may envelop an entire region of the first electrode line except for the portion of the first electrode line exposed through the first opening and envelop an entire region of the second electrode line except for the portion of the second electrode line exposed through the second opening.

The pulse sensing module may further include an attachment medium layer bonded to the other surface of the piezoelectric layer such that the attachment medium layer maintains a shape of the piezoelectric layer to be stably attached to a bending module of the blood pressure measuring device, wherein the bending module is bendable such that accuracy of the voltage signal for the pulse generated by the piezoelectric effect of the piezoelectric layer is improved, thereby allowing the blood pressure measuring device to be tightly attached to a curved skin surface of the human body.

The attachment medium layer may be bendable to be linked with bending of the bending module, thereby blocking the piezoelectric layer from being separated from the bending module.

According to another embodiment of the present disclosure, there is provided a blood pressure measuring device attached to the skin such that at least one of systolic pressure, diastolic pressure, and blood pressure variation is measured, which includes: the pulse sensing module; and a blood pressure calculation module that calculates the at least one of the systolic pressure, the diastolic pressure, and the blood pressure variation using a voltage signal generated by the piezoelectric effect, wherein the blood pressure calculation module extracts a maximum voltage value $V_{Max}$ and a minimum voltage value $V_{Min}$ of the voltage signal that is obtained by the pulse sensing module and corresponds to each pulse signal for a predetermined time and then calculates the at least one of the systolic pressure, the diastolic pressure, and the blood pressure variation on the basis of the extracted maximum voltage value $V_{Max}$ and minimum voltage value $V_{Min}$.

The blood pressure calculation module may calculate a maximum voltage average value $V_{Max,Avg}$, which is an average value for the maximum voltage value $V_{Max}$ extracted from the voltage signal for each pulse signal and calculate a voltage variation average value $\Delta V_{Avg}$, which is an average value for the difference between the maximum voltage value $V_{Max}$ and the minimum voltage value $V_{Min}$ extracted from the voltage signal for each pulse signal to calculate the at least one of the systolic pressure, the diastolic pressure, and the blood pressure variation.

The blood pressure calculation module may calculate, on the basis of a relationship based on big data analysis, the systolic pressure and blood pressure variation $\Delta P$ from each of the maximum voltage average value $V_{Max,Avg}$ and the voltage variation average value $\Delta V_{Avg}$.

A relationship between the maximum voltage average value $V_{Max,Avg}$ and the systolic pressure $P_{systolic}$ on the basis of the big data analysis may satisfy the following Conditional Expression 1:

$$P_{systolic} = \frac{V_{Max,Avg} - \beta}{\alpha}, \qquad \text{<Conditional Expression 1>}$$

where $P_{systolic}$ is systolic pressure, $V_{Max,Avg}$ is a maximum voltage average value, and $\alpha$ and $\beta$ are constants that are derived by using big data analysis.

A relationship between the voltage variation average value $\Delta V_{Avg}$ and the blood pressure variation $\Delta P$ on the basis of the big data analysis may satisfy the following Conditional Expression 2:

$$\Delta P = -\gamma \times \Delta V_{Avg} + \delta, \qquad \text{<Conditional Expression 2>}$$

where $\Delta P$ is blood pressure variation, $\Delta V_{Avg}$ is a voltage variation average value, and $\gamma$ and $\delta$ are constants that are derived by using big data analysis.

The blood pressure calculation module may subtract the blood pressure variation $\Delta P$ from the systolic pressure $P_{systolic}$ to calculate the diastolic pressure $P_{diastolic}$.

The blood pressure calculation module may include: a signal preprocessing unit that amplifies an amplitude of the voltage signal generated by the piezoelectric effect and filters noise; a conversion unit that converts, to a digital signal, the voltage signal pre-processed by the signal pre-processing unit and outputs the digital signal; and a control unit that calculates the at least one of the systolic pressure, the diastolic pressure, and the blood pressure variation on the basis of the voltage signal converted by the conversion unit.

The blood pressure measuring device may further include a bending module that has the pulse sensing module and the blood pressure calculation module attached thereto and is bendable to allow the blood pressure measuring device to be tightly attached to a curved skin surface of the human body.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1A:
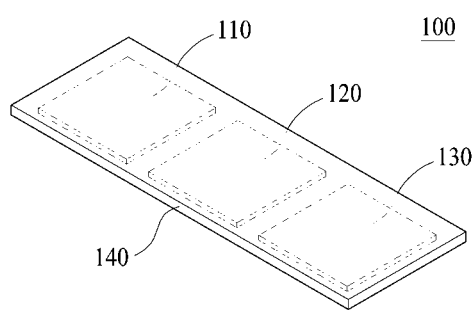
FIG. 1A is a schematic perspective view showing a blood pressure measuring device according to an embodiment of the present disclosure.

Hereinafter, specific embodiments of the present disclosure will be described in detail with reference to the accompanying drawings.

Meanwhile, the spirit of the present disclosure is not limited to the suggested embodiments, and those skilled in the art to which the present disclosure pertains could easily suggest a further retrogressive invention or another embodiment which falls within the spirit of the present disclosure through the addition, modification, and deletion of another component without departing from the spirit of the present disclosure.

In the following description, components having the same function within the same scope illustrated in the drawings of the embodiments are illustrated using the same reference numerals.

1. Overview of Blood Pressure Measuring Device

Figure 1B:
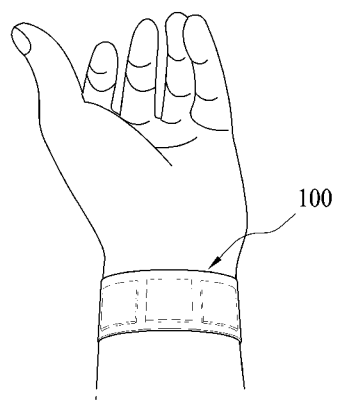
FIG. 1B is a view illustrating a situation in which the blood pressure measuring device according to an embodiment of the present disclosure is worn on a wrist to be used for measuring blood pressure.
Figure 2:
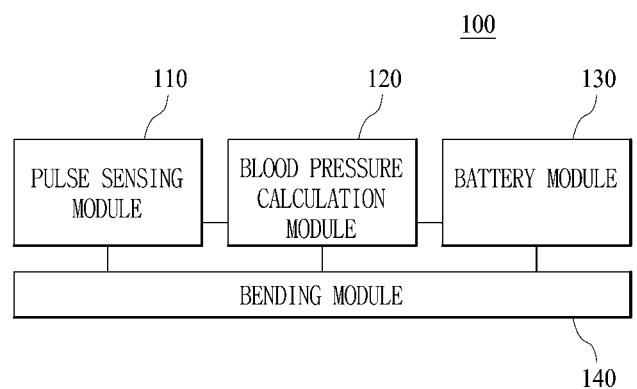
FIG. 2 is a block diagram illustrating the blood pressure measuring device according to the embodiment of the present disclosure.

FIG. 1A is a schematic perspective view showing a blood pressure measuring device according to an embodiment of the present disclosure. FIG. 1B is a view illustrating a situation in which the blood pressure measuring device according to an embodiment of the present disclosure is worn on a wrist to be used for measuring blood pressure. FIG. 2 is a block diagram illustrating the blood pressure measuring device according to the embodiment of the present disclosure.

Referring to FIGS. 1A, 1B and 2, a blood pressure measuring device 100 according to the embodiment of the present disclosure is attached to the skin to measure at least one of systolic pressure, diastolic pressure, and blood pressure variation and may be manufactured as a patch or band type device that is attached to a part of the human body in which a pulse is detectable.

The blood pressure measuring device 100 is manufactured as a band type device that is wearable on the wrist as illustrated in FIG. 1B, and an example of the blood pressure measuring device 100 manufactured as the band type device will be described hereinafter.

The blood pressure measuring device 100 may measure blood pressure using a voltage signal generated by a mechanical pressure due to a pulse and may include a pulse sensing module 110 for implementing such a piezoelectric effect.

The pulse sensing module 110 may detect a testee's pulse signal to generate a voltage signal that corresponds to the pulse signal, and the voltage signal is amplified, filtered, and digitized to be usable for calculating systolic pressure, diastolic pressure, and blood pressure variation.

The above operation for the voltage signal may be performed by a blood pressure calculation module 120, and the blood pressure calculation module 120 may be electrically connected to the pulse sensing module 110 for analysis of the voltage signal.

The blood pressure calculation module 120 may calculate the systolic pressure, the diastolic pressure, and the blood pressure variation from the voltage signal through a conditional expression derived on the basis of big data analysis.

Meanwhile, the blood pressure measuring device 100 may include a battery module 130 for driving the blood pressure calculation module 120.

The battery module 130 may include a battery, such as a lithium battery, that is capable of supplying power and being charged or discharged, but the type of the battery module 130 is not limited thereto. Any battery for driving the blood pressure calculation module 120 is usable.

The battery module 130 may include elements for charging the battery, for example, a charging integrated circuit (IC) or the like for constant current charging.

Further, when it is required to boost or reduce an output voltage of the battery for driving the blood pressure calculation module 120, the battery module 130 may include a boosting circuit and a converting circuit for implementing this operation.

For example, when a driving voltage of 3 V or 5 V is required as the output voltage of the battery, the battery module 130 may include a boosting circuit for boosting 3 V to 5 V and a converting circuit for converting 5 V to −5 V.

Meanwhile, the blood pressure measuring device 100 is manufactured as the patch or band type device as mentioned above to be attachable to the part in which the pulse is detectable and may include a bending module 140 that is bendable such that accuracy of blood pressure measurement is improved when the part is a curved skin surface, thereby allowing the blood pressure measuring device 100 to be tightly attached to the curved skin surface.

The pulse sensing module 110, the blood pressure calculation module 120, and the battery module 130 are attachable to the bending module 140, and the bending module 140 may be an element for supporting the above elements.

The bending module 140 may be formed of a rubber material, a synthetic material, or the like that is bendable to surround the wrist and has flexibility and bendability. For example, the bending module 140 may be formed of polyimide, polyester, or the like.

Further, the bending module 140 may also be formed of a material that has properties of returning to an original shape thereof with a predetermined level of elasticity.

The pulse sensing module 110 and the blood pressure calculation module 120 may have a predetermined level of flexibility as the bending module 140. Thus, the blood pressure measuring device 100 according to the embodiment of the present disclosure may improve accuracy of a voltage signal due to a piezoelectric effect, thereby significantly increasing precision of blood pressure measurement.

Meanwhile, FIG. 1A shows the blood pressure measuring device 100 according to the present disclosure in which a cover having flexibility provides the exterior thereof. However, the cover is not an essential element, and the bending module 140 may provide the exterior. At least one of the pulse sensing module 110, the blood pressure calculation module 120, and the battery module 130 may be manufactured to be exposed.

The pulse sensing module 110 and the blood pressure calculation module 120, which are elements for measuring blood pressure by using the blood pressure measuring device 100, will hereinafter be described in detail.

2. Pulse Sensing Module and Method of Manufacturing Same

Figure 3:
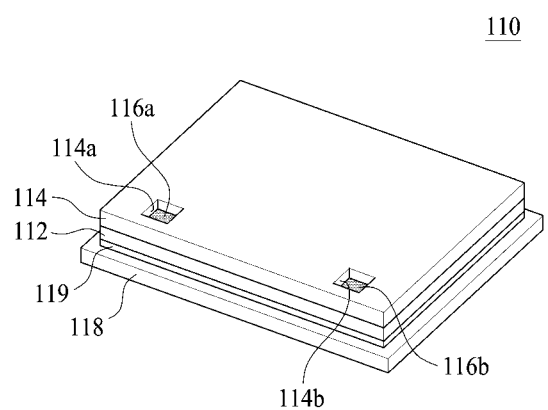
FIG. 3 is a schematic perspective view showing a pulse sensing module according to the present disclosure.
Figure 4:
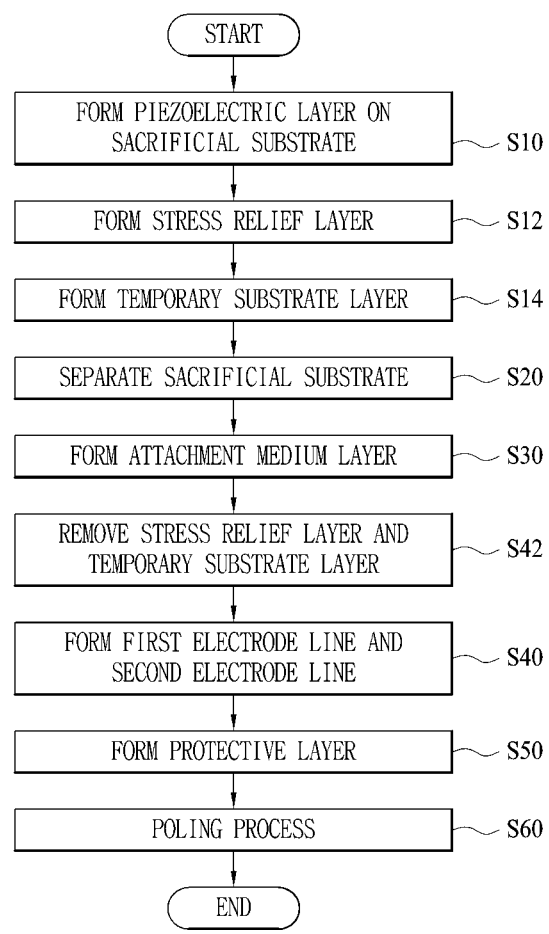
FIG. 4 is a flowchart illustrating a method of manufacturing a pulse sensing module according to the present disclosure.

FIG. 3 is a schematic perspective view showing the pulse sensing module according to the present disclosure. FIG. 4 is a flowchart illustrating a method of manufacturing a pulse sensing module according to the present disclosure. FIGS. 5 to 13 are views illustrating the method of manufacturing a pulse sensing module according to the present disclosure.

Referring first to FIG. 3, the pulse sensing module 110 according to the present disclosure is an element for generating a voltage signal by a mechanical pressure due to a pulse and may include a piezoelectric layer 112 and a protective layer 114.

The piezoelectric layer 112 may be a piezoelectric thin film that is composed of a piezoelectric material for generating a piezoelectric effect due to a pulse, and a first electrode line 116a and a second electrode line 116b spaced apart from each other may be formed as a pattern on one surface of the piezoelectric layer 112.

The protective layer 114 is an element that is applied to the piezoelectric layer 112 to protect the piezoelectric layer 112 and may include openings 114a and 114b that allow a portion of the first electrode line 116a and a portion of the second electrode line 116b to be exposed.

The openings 114a and 114b enable a poling process of applying a high voltage to the first electrode line 116a and the second electrode line 116b to improve the polarity of the piezoelectric material and may allow the first electrode line 116a and the second electrode line 116b to be electrically connected to the blood pressure calculation module 120.

The openings 114a and 114b may include a first opening 114a and a second opening 114b that are formed in positions corresponding to those of an end portion of the first electrode line 116a and an end portion of the second electrode line 116b.

The protective layer 114 may be formed of an epoxy that may be cured by ultraviolet (UV) light, and may be, for example, SU-8-based negative photoresist that is composed of bisphenol A Novolacs (phenol-formaldehyde)-based epoxy.

The protective layer 114 may envelop an entire region of the first electrode line 116a except for the portion of the first electrode line 116a exposed through the first opening 114a and envelop an entire region of the second electrode line 116b except for the portion of the second electrode line 116b exposed through the second opening 114b.

Meanwhile, the pulse sensing module 110 may include an attachment medium layer 118 that is bonded to the other surface of the piezoelectric layer 112 such that the attachment medium layer 118 maintains the shape of the piezoelectric layer 112 to be stably attached to the bending module 140 of the blood pressure measuring device 100.

The attachment medium layer 118 may be formed of poly(ethyl benzene-1,4-dicarboxylate) (PET) or polyethylene naphthalate (PEN) which is generally a transparent plastic substrate.

The attachment medium layer 118 may be attached to the other surface of the piezoelectric layer 112 by the medium of a bonding layer 119 and is bendable to be linked with bending of the bending module 140, thereby blocking the piezoelectric layer 112 from being separated from the bending module 140.

The bonding layer 119 may be, for example, a Norland optical adhesive (NOA) solution product that is cured by UV light and may be formed by being applied by spin coating.

In this case, the blood pressure measuring device 100 may be manufactured as the patch or band type device to be attachable to the part in which the pulse is detectable and may be in close contact with the curved skin surface due to the bending module 140 having flexibility and bendability even when the part is a curved skin surface.

The attachment medium layer 118 is also flexible and bendable. When the bending module 140 is bent, the attachment medium layer 118 may be bent by being linked with the bending of the bending module 140, thereby being prevented from being separated from the bending module 140. As a result, the piezoelectric layer 112 may be prevented from being separated from the bending module 140.

A method of manufacturing the pulse sensing module 110 will be described hereinafter.

Referring to FIG. 4, the method of manufacturing the pulse sensing module 110 may include a first operation S10 of forming the piezoelectric layer 112 on one surface of a sacrificial substrate 200 using the piezoelectric material, a second operation S20 of separating the sacrificial substrate 200 from the piezoelectric layer 112, a third operation S30 of forming the attachment medium layer 118 on the one surface of the piezoelectric layer 112 from which the sacrificial substrate 200 is separated such that the attachment medium layer 118 maintains the shape of the piezoelectric layer 112 to be stably attached to the bending module 140 of the blood pressure measuring device 100, a fourth operation S40 of forming, on the other surface of the piezoelectric layer 112, the first electrode line 116a and the second electrode line 116b that are spaced apart from each other, and a fifth operation S50 of forming the protective layer 114 on the other surface of the piezoelectric layer 112 on which the first electrode line 116a and the second electrode line 116b are formed.

In this case, the first operation S10 may include an operation S12 of forming a stress relief layer 300 and an operation S14 of forming a temporary substrate layer 400. The fourth operation S40 may include an operation S42 of removing the stress relief layer 300 and the temporary substrate layer 400, which is performed before forming the first electrode line 116a and the second electrode line 116b.

Meanwhile, the method of manufacturing the pulse sensing module 110 may further include a sixth operation S60 of performing a poling process of applying a high voltage to the first electrode line 116a and the second electrode line 116b to improve the polarity of the piezoelectric material.

The operations will hereinafter be described in detail with reference to FIGS. 5 to 13, and it should be noted that the drawings are exaggerated for convenience of explanation.

Figure 5:
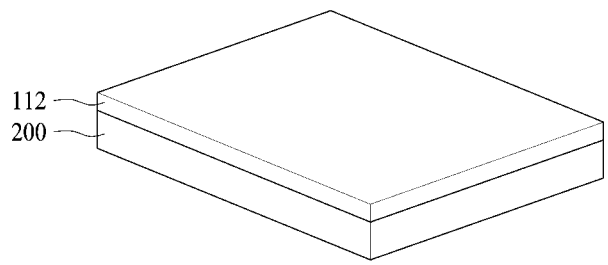
FIGS. 5 to 13 are views illustrating the method of manufacturing a pulse sensing module according to the present disclosure.

Referring to FIG. 5, the first operation S10 of forming the piezoelectric layer 112, which is a piezoelectric thin film, on the one surface of the sacrificial substrate 200 using the piezoelectric material may be performed first.

The sacrificial substrate 200 may be formed of quartz or sapphire that is transparent and withstands a high-temperature heat treatment and may be an element that is required to form the piezoelectric layer 112 by growing the piezoelectric thin film formed of the piezoelectric material.

For example, the sacrificial substrate 200 may be formed of $Al_2O_3$-based sapphire that has a structure similar to a crystal structure of the piezoelectric thin film for the growth of the piezoelectric thin film.

The piezoelectric material has a perovskite structure and may be lead zirconate titanate (PZT) or the like but is not limited thereto.

A variety of known methods may be applicable to the method of forming the piezoelectric layer 112, which is a piezoelectric thin film, using the piezoelectric material, and may be, for example, deposition methods such as direct current/radio frequency (DC/RF) sputtering, aerosol deposition, a sol-gel solution process (a heat treatment after spin coating), and screen/inkjet printing.

The sacrificial substrate 200 may be separated from the piezoelectric layer 112, which is a piezoelectric thin film, by a laser lift off (LLO) method during the second operation S20. To this end, the sacrificial substrate 200 may be formed as a transparent substrate that may transmit light.

Figure 6:
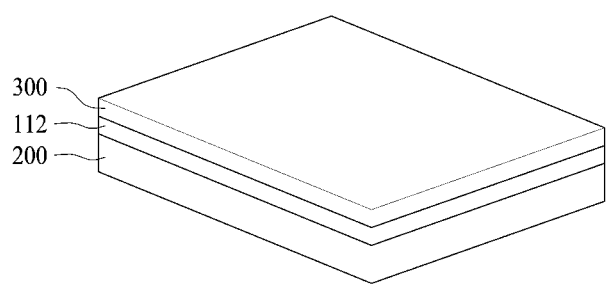

Referring to FIG. 6, after the piezoelectric layer 112 is formed on the one surface of the sacrificial substrate 200, the operation S12 of forming the stress relief layer 300 on the other surface, which is opposite to the one surface of the piezoelectric layer 112 having the sacrificial substrate 200 formed thereon, in order to relieve stress which may occur in a subsequent process and which is caused by at least one of high temperature, high pressure, and impact may be performed.

The stress relief layer 300 may be an element for preventing a degradation in piezoelectric characteristics or inaccuracy of an output voltage that results from a structural or material modification, such as cracking or wrinkling, of the piezoelectric layer 112, which is a piezoelectric thin film, by stress due to a mechanical, physical, or thermal external force caused by high temperature, high pressure, or impact during the second operation S20 of removing the sacrificial substrate 200.

The stress relief layer 300 may be formed of an epoxy, for example, bisphenol A Novolacs (phenol-formaldehyde)-based epoxy, that is cured by UV light, and a thickness of the stress relief layer 300 of 500 nm or more may be sufficient.

Figure 7:
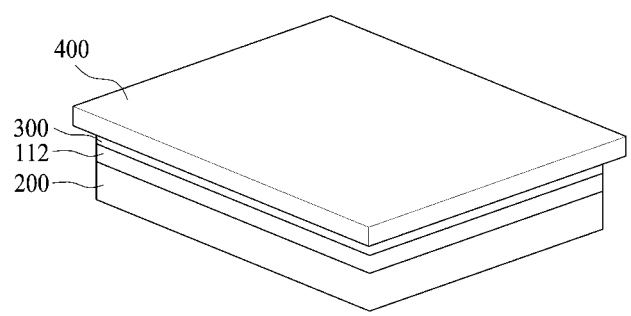

Referring to FIG. 7, when the stress relief layer 300 is formed, the operation S14 of forming the temporary substrate layer 400 on one surface of the stress relief layer 300 for handling of the piezoelectric layer 112 in a subsequent operation may be performed.

The temporary substrate layer 400 is necessary because, when the second operation S20, which is a subsequent operation, is performed so that the sacrificial substrate 200 is separated from the piezoelectric layer 112, a thickness of the entire layer excluding the temporary substrate layer 400 becomes about several µm, and when an operation subsequent to the second operation S20 is performed with only the thickness excluding that of the temporary substrate layer 400, it is virtually impossible to handle the piezoelectric layer 112, which is a piezoelectric thin film.

Of course, the operation S12 of forming the stress relief layer 300 as a single layer capable of simultaneously performing the function of the stress relief layer 300 and the function of the temporary substrate layer 400 and the operation S14 of forming the temporary substrate layer 400 may also be performed as one operation.

The temporary substrate layer 400 may be formed of a material that may be removed by heat or UV light.

For example, the temporary substrate layer 400 may be tape that has a thermally expandable adhesive or a UV energy beam expandable adhesive applied on one or both surfaces thereof, and the adhesive may have properties of being easily expanded by heat or UV light to be vaporized.

The adhesive has a structure in which particles having a spherical or other shape are included in a matrix material. The matrix material is a thermoplastic material such as polyvinyl alcohol, polyvinyl butyral, polyacrylonitrile, or polysulfone and may have the properties of being melted and expanded by heat to be ruptured. The particles present therein are thermally expandable particles that have a structure such as that of isobutene, propane, or pentane, may have a diameter of about 500 nm to about 100 µm and may include one thereof or a combination of two or more thereof.

The adhesive as described above may be applied to the one or both surfaces of the tape, and a thickness of the temporary substrate layer 400 may be, for example, 1 to 500 µm.

Figure 8:
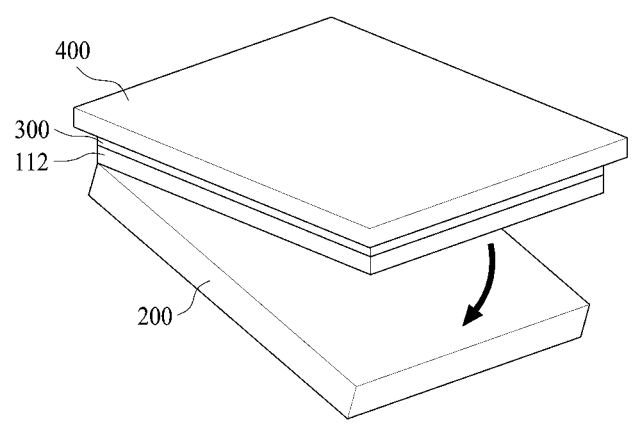

Referring to FIG. 8, after the stress relief layer 300 and the temporary substrate layer 400 are formed by the first operation S10, the second operation S20 of separating the sacrificial substrate 200 from the piezoelectric layer 112 may be performed.

A method of separating the sacrificial substrate 200 from the piezoelectric layer 112 may include a mechanical separation method, a chemical etching method, or the aforementioned LLO method.

For example, when the method of separating the sacrificial substrate 200 from the piezoelectric layer 112 is the LLO method, the sacrificial substrate 200 is formed as a transparent substrate that may transmit light and that may be removed by light energy transmitted through the transparent substrate.

Figure 9:
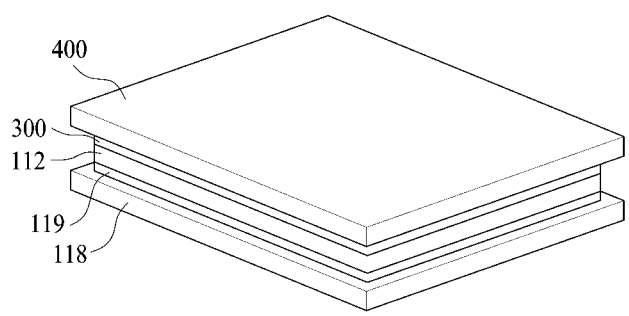

Referring to FIG. 9, the third operation S30 of forming the attachment medium layer 118 on the one surface of the piezoelectric layer 112 from which the sacrificial substrate 200 is separated such that the attachment medium layer 118 maintains the shape of the piezoelectric layer 112 to be stably attached to the bending module 140 of the blood pressure measuring device 100 may be performed.

The attachment medium layer 118 may be attached to the other surface of the piezoelectric layer 112 by the medium of the bonding layer 119.

The bonding layer 119 may be, for example, a NOA solution product that is cured by UV light and may be formed by being applied by spin coating.

The attachment medium layer 118 is flexible and bendable. Thus, when the blood pressure measuring device 100 is tightly attached to the curved skin surface for blood pressure measurement, the attachment medium layer 118 is bent by being linked with the bending of the bending module 140 that has flexibility and bendability, thereby being prevented from being separated from the bending module 140. As a result, the piezoelectric layer 112 may be prevented from being separated from the bending module 140.

Figure 10:
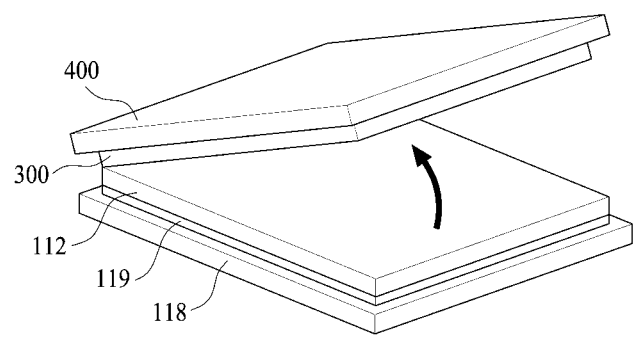
Figure 11:
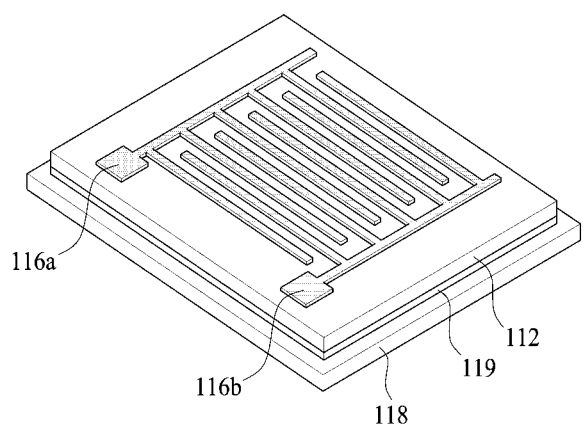

Referring to FIGS. 10 and 11, the fourth operation S40 of forming the first electrode line 116a and the second electrode line 116b that are spaced apart from each other on the other surface of the piezoelectric layer 112 may be performed.

As illustrated in FIG. 10, the operation S42 of removing the stress relief layer 300 and the temporary substrate layer 400 before forming the first electrode line 116a and the second electrode line 116b may be performed, and this operation may be performed through a process of applying heat or UV light to the stress relief layer 300 and the temporary substrate layer 400.

When the heat or UV light is applied to the stress relief layer 300 and the temporary substrate layer 400, the adhesive included in the temporary substrate layer 400 is expanded and vaporized to be reduced in adhesive force, and then the stress relief layer 300 and the temporary substrate layer 400 may be removed through a physical separation operation.

In this case, since the stress relief layer 300 is in a previously cured state, adhesion with other layers does not increase even with the application of heat or UV light thereto, and even when heat or UV light is applied to the temporary substrate layer 400 so that an adhesive component thereof is expanded and vaporized, the adhesive force remains sufficient to separate the temporary substrate layer 400 by the physical separation operation.

The adhesive force of the temporary substrate layer 400 sufficient to separate the same by the physical separation operation becomes higher than that by which the stress relief layer 300 is bonded to the piezoelectric layer 112. Thus, the stress relief layer 300 may be simultaneously removed during the physical separation operation on the temporary substrate layer 400.

However, the stress relief layer 300 and the temporary substrate layer 400 do not need to be removed at the same time and may be sequentially removed.

When the stress relief layer 300 and the temporary substrate layer 400 are removed as illustrated in FIG. 10, the first electrode line 116a and the second electrode line 116b spaced apart from each other are formed on the other surface of the piezoelectric layer 112, as illustrated in FIG. 11.

The first electrode line 116a and the second electrode line 116b may be formed as a pattern through a known semiconductor process after application of an electrode material.

The first electrode line 116a and the second electrode line 116b may include a plurality of parallel lines that are disposed parallel to a main line, but the arrangement of the lines may be variously changed.

Figure 12:
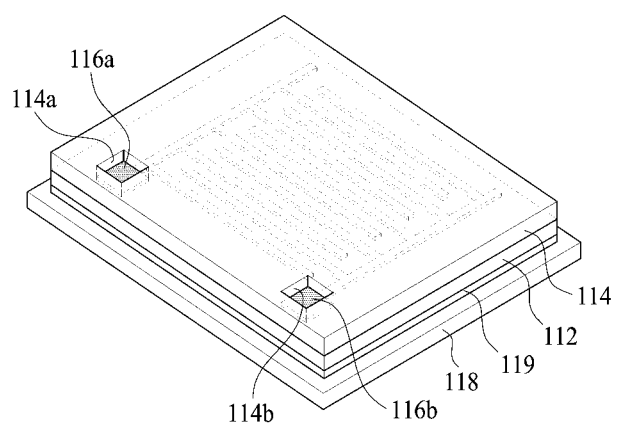

Referring to FIG. 12, after the first electrode line 116a and the second electrode line 116b are formed, the fifth operation S50 of forming the protective layer 114 on the other surface of the piezoelectric layer 112 on which the first electrode line 116a and the second electrode line 116b are formed, such that the piezoelectric layer 112 is protected may be performed.

The protective layer 114 has the first opening 114a and the second opening 114b so as to expose the end portion of the first electrode line 116a and the end portion of the second electrode line 116b.

In this case, the exposed end portions of the first and second electrode lines 116a and 116b enable the poling process that is to be performed in a subsequent operation and may be used as elements for an electrical connection with the blood pressure calculation module 120 for blood pressure measurement.

Figure 13:
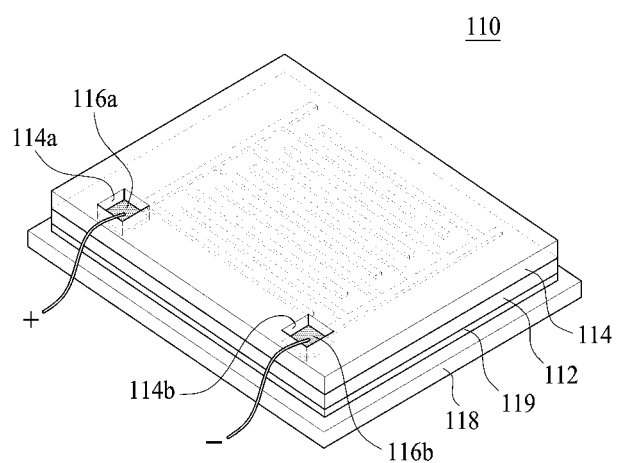

Referring to FIG. 13, when the formation of the protective layer 114 is completed, the sixth operation S60, which is a poling process of applying a high voltage to the first electrode line 116a and the second electrode line 116b to improve the polarity of the piezoelectric material, may be performed.

The poling process provides dipole directionality to the piezoelectric material and may be performed by applying an electric field of, for example, 100 kV/cm for at least 2 hours, but the method of performing the poling process is not limited thereto.

As described above, the poling process of the sixth operation S60, for example, a process of applying a high voltage through the first opening 114a and the second opening 114b of the protective layer 114 may significantly increase polarity efficiency of the piezoelectric layer 112 while sufficiently protecting the pulse sensing module 110 physically.

In other words, when a high voltage is applied and the protective layer 114 is not present, an electric field effect between electrodes causes an electric current to flow therebetween so that the electrodes are disconnected. However, the present disclosure allows the protective layer 114 having the first opening 114a and the second opening 114b such that a high voltage may be applied to offset the electric field effect between the electrodes to solve the above problem, thereby improving polarity efficiency of the piezoelectric layer 112.

When the first to sixth operations S10 to S60 are completed as described above, manufacturing of the pulse sensing module 110 constituting the blood pressure measuring device 100 is completed.

3. Blood Pressure Calculation Module

Figure 14:
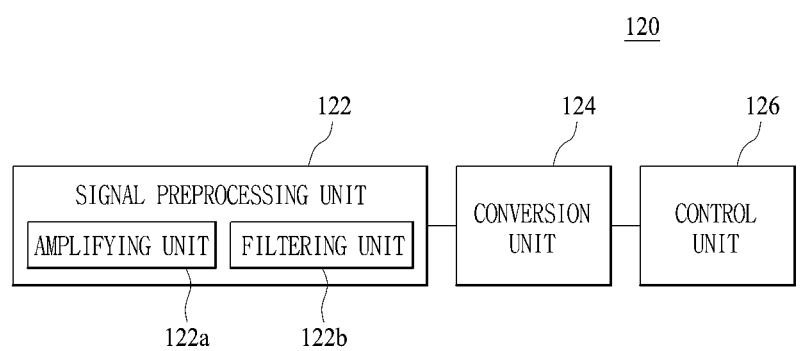
FIG. 14 is a block diagram illustrating a blood pressure calculation module according to the present disclosure.
Figure 15:
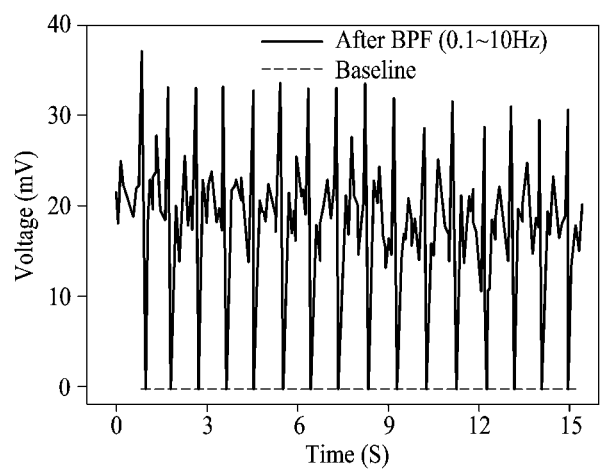
FIG. 15 is a time vs. voltage signal graph showing a state in which a voltage signal is amplified and filtered by the blood pressure calculation module according to the present disclosure.

FIG. 14 is a block diagram illustrating a blood pressure calculation module according to the present disclosure. FIG. 15 is a time vs. voltage signal graph showing a state in which a voltage signal is amplified and filtered by the blood pressure calculation module according to the present disclosure.

Figure 16:
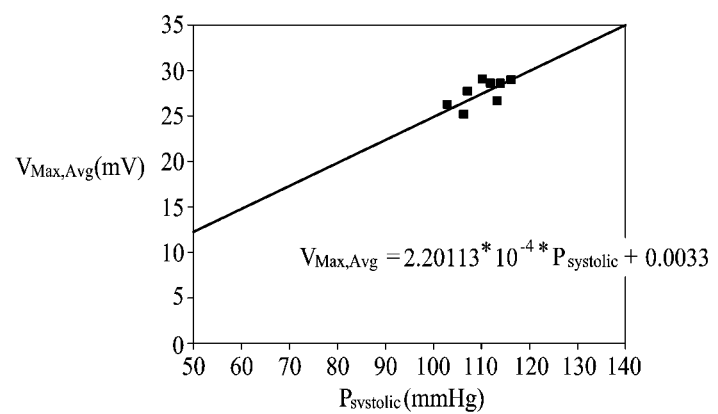
FIG. 16 is a graph illustrating the relationship between a maximum voltage average value $V_{Max,Avg}$ and systolic pressure $P_{systolic}$ on the basis of big data analysis.
Figure 17:
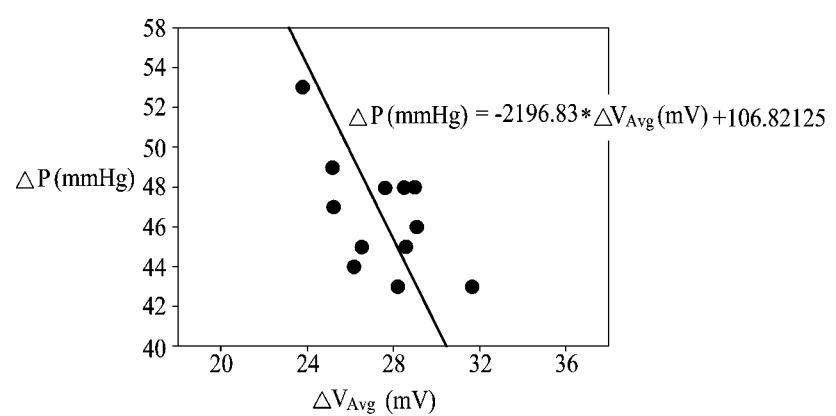
FIG. 17 is a graph illustrating the relationship between a voltage variation average value $\Delta V_{Avg}$ and blood pressure variation $\Delta P$ on the basis of big data analysis.

In addition, FIG. 16 is a graph illustrating the relationship between a maximum voltage average value $V_{Max,Avg}$ and systolic pressure $P_{systolic}$ on the basis of big data analysis. FIG. 17 is a graph illustrating the relationship between a voltage variation average value $\Delta V_{Avg}$ and blood pressure variation $\Delta P$ on the basis of big data analysis.

Referring first to FIGS. 14 to 17, the blood pressure calculation module 120 according to the present disclosure may calculate at least one of systolic pressure, diastolic pressure, and blood pressure variation using a voltage signal due to a piezoelectric effect that is provided through the pulse sensing module 110 electrically connected to the blood pressure calculation module 120.

The blood pressure calculation module 120 may fundamentally include a flexible printed circuit board (FPCB), and the FPCB may have a chip or the like that is mounted thereon to perform functions to be described below or a circuit that is patterned thereon.

The FPCB may be attached to the bending module 140. Thus, when the blood pressure measuring device 100 is tightly attached to the curved skin surface for blood pressure measurement, the blood pressure measuring device 100 may be bent by being linked with the bending of the bending module 140 that has flexibility and bendability.

An electrical connection between the pulse sensing module 110 and the blood pressure calculation module 120 may be implemented by interconnecting, with a terminal of the FPCB, the end portion of the first electrode line 116a and the end portion of the second electrode line 116b, which are exposed through the first opening 114a and the second opening 114b of the protective layer 114, using a conductive material. The conductive material may be a metallic material that has a resistance less than or equal to 10 Ω.

Meanwhile, the blood pressure calculation module 120 may include a signal preprocessing unit 122 that receives the voltage signal provided by the pulse sensing module 110, amplifies the amplitude of the voltage signal, and filters the noise, a conversion unit 124 that converts, to a digital signal, the voltage signal pre-processed by the signal preprocessing unit 122 and outputs the digital signal, and a control unit 126 that calculates the at least one of the systolic pressure, the diastolic pressure, and the blood pressure variation on the basis of the voltage signal converted by the conversion unit 124.

In this case, the signal preprocessing unit 122 may include an amplifying unit 122a and a filtering unit 122b, the amplifying unit 122a may amplify the voltage signal provided by the pulse sensing module 110, and the filtering unit 122b may filter the noise included in the amplified voltage signal.

FIG. 15 is a time vs. voltage signal graph showing a state in which a voltage signal generated by a mechanical pressure due to a pulse is amplified by the amplifying unit 122a and the noise is filtered by the filtering unit 122b.

The conversion unit 124 is an element that converts the voltage signal, which is amplified by the amplifying unit 122a and of which the noise is filtered by the filtering unit 122b, and may be an analog-to-digital converter (ADC) that converts an analog voltage signal to a digital signal and outputs the digital signal in the form of a voltage signal that the control unit 126 may recognize.

Meanwhile, the control unit 126 may calculate the at least one of the systolic pressure, the diastolic pressure, and the blood pressure variation on the basis of the voltage signal converted to the digital signal through the conversion unit 124, which will be described below in detail.

When the testee wears the blood pressure measuring device 100 on the wrist and requests blood pressure measurement therefrom, the pulse sensing module 110 detects a pulse signal for a predetermined time in response to the request and transmits, to the blood pressure calculation module 120, the voltage signal due to the piezoelectric effect.

In this case, the predetermined time may be, for example, 15 seconds, as illustrated in FIG. 15, but the present disclosure is not limited thereto and may be variously changed.

The control unit 126 may extract a maximum voltage value $V_{Max}$ and a minimum voltage value $V_{Min}$ of a voltage signal that corresponds to each pulse signal for the predetermined time, may calculate a maximum voltage average value $V_{Max,Avg}$, which is an average value for the maximum voltage value $V_{Max}$ extracted from the voltage signal for each pulse signal, and may calculate a voltage variation average value $\Delta V_{Avg}$, which is an average value for the difference between the maximum voltage value $V_{Max}$ and the minimum voltage value $V_{Min}$ extracted from the voltage signal for each pulse signal.

Conditional Expression 1 and Conditional Expression 2 for calculating the maximum voltage average value $V_{Max,Avg}$ and the voltage variation average value $\Delta V_{Avg}$ are as follows:

$$V_{Max,Avg} = \Sigma \frac{V_{Max}}{n} = \sum_{i=1}^{n} \frac{V_{i,Max}}{n}; \text{ and} \qquad \text{<Conditional Expression 1>}$$

$$\Delta V_{Avg} = \sum_{i=1}^{n} \frac{V_{i,Max} - V_{i,Min}}{n}. \qquad \text{<Conditional Expression 2>}$$

In this case, n is the number of pulse signals, which may be 16 in the case of FIG. 15.

After calculating the maximum voltage average value $V_{Max,Avg}$ and the voltage variation average value $\Delta V_{Avg}$ through Conditional Expression 1 and Conditional Expression 2, the control unit 126 calculates the systolic pressure $P_{systolic}$ and the blood pressure variation $\Delta P$ from the maximum voltage average value $V_{Max,Avg}$ and the voltage variation average value $\Delta V_{Avg}$, respectively, on the basis of the relationship based on big data analysis.

In this case, the big data analysis for calculating the systolic pressure $P_{systolic}$ may be obtained by comparing and analyzing the relationship between the maximum voltage average value $V_{Max,Avg}$ and the systolic pressure $P_{systolic}$ among information of the testee that is collected and stored in big data form, and FIG. 16 shows the relationship between the maximum voltage average value $V_{Max,Avg}$ and the systolic pressure $P_{systolic}$ by using big data analysis on a normal person.

Referring to FIG. 16, the relationship between the maximum voltage average value $V_{Max,Avg}$ and the systolic pressure $P_{systolic}$ by using the big data analysis in the case of the normal person is as shown in the following Conditional Expression 3:

$$V_{Max,Avg} = 2.20113 \times 10^{-4} \cdot P_{systolic} + 0.0033. \qquad \text{<Conditional Expression 3>}$$

Thus, when Conditional Expression 3 is generalized, the relationship between the maximum voltage average value $V_{Max,Avg}$ and the systolic pressure $P_{systolic}$ may be generalized by the following Conditional Expression 4:

$$P_{systolic} = \frac{V_{Max,Avg} - \beta}{\alpha}, \qquad \text{<Conditional Expression 4>}$$

where $P_{systolic}$ is systolic pressure, $V_{Max,Avg}$ is a maximum voltage average value, $\alpha$ and $\beta$ are constants that are derived by using big data analysis, and in the case of the normal person, $\alpha$ is $2.20113 \times 10^{-4}$, and $\beta$ is 0.0033.

Further, the big data analysis for calculating the blood pressure variation $\Delta P$ may be obtained by comparing and analyzing the relationship between the voltage variation average value $\Delta V_{Avg}$ and the blood pressure variation $\Delta P$ among the information of the testee that is collected and stored in big data form, and FIG. 17 shows the relationship between the voltage variation average value $\Delta V_{Avg}$ and the blood pressure variation $\Delta P$ by using big data analysis on a normal person.

Referring to FIG. 17, the relationship between the voltage variation average value $\Delta V_{Avg}$ and the blood pressure variation $\Delta P$ by the big data analysis in the case of the normal person is as shown in the following Conditional Expression 5:

$$\Delta P(\text{mmHg}) = -2196.83 \cdot \Delta V_{Avg}(\text{mV}) + 106.82125. \qquad \text{<Conditional Expression 5>}$$

Thus, when Conditional Expression 5 is generalized, the relationship between the voltage variation average value $\Delta V_{Avg}$ and the blood pressure variation $\Delta P$ may be generalized by the following Conditional Expression 6:

$$\Delta P = -\gamma \times \Delta V_{Avg} + \delta, \qquad \text{<Conditional Expression 6>}$$

where $\Delta P$ is blood pressure variation, $\Delta V_{Avg}$ is a voltage variation average value, $\gamma$ and $\delta$ are constants that are derived by using big data analysis, and in the case of the normal person, $\gamma$ is 2196.83, and $\delta$ is 106.82125.

Meanwhile, $\alpha$, $\beta$, $\gamma$, and $\delta$ used in Conditional Expressions 4 and 6 may vary according to the characteristics of the testee that are collected and stored in big data form and may be constants that may vary according to, for example, high blood pressure, low blood pressure, disease group, age, and sex.

The control unit 126 may calculate the diastolic pressure $P_{diastolic}$ by subtracting the blood pressure variation $\Delta P$ from the systolic pressure $P_{systolic}$, as in the following Conditional Expression 7:

$$P_{diastolic} = P_{systolic} - \Delta P \qquad \text{<Conditional Expression 7>}$$

As described above, the blood pressure calculation module 120 according to the present disclosure amplifies and filters the voltage signal due to the piezoelectric effect that is provided through the pulse sensing module 110 electrically connected to the blood pressure calculation module 120, converts the voltage signal to a digital signal, and ultimately calculates the systolic pressure and the diastolic pressure through a series of processing operations, thereby enabling the blood pressure measurement of the testee.

Further, accuracy of the blood pressure measurement may be improved by measuring blood pressure using the relationship between the maximum voltage average value $V_{Max,Avg}$ and the systolic pressure $P_{systolic}$ and the relationship between the voltage variation average value $\Delta V_{Avg}$ and the blood pressure variation $\Delta P$, which are derived by using big data analysis.

The blood pressure measuring device 100, according to the embodiment of the present disclosure, may be manufactured as a patch or band type device that is attachable to the skin, thereby providing convenience in blood pressure measurement to a tester and the testee.

Meanwhile, the blood pressure measuring device 100 according to the present disclosure may further include a display module that displays the systolic pressure and the diastolic pressure calculated by the control unit 126.

Further, the blood pressure measuring device 100 according to the present disclosure may further include a device interface for supporting interfacing with an external device such that the systolic pressure and the diastolic pressure calculated by the control unit 126 may be displayed through the external device.

4. Method of Measuring Blood Pressure using Blood Pressure Measuring Device and Recording Medium on which Program for Performing Method is Stored FIG. 18 is a flowchart illustrating a method of measuring blood pressure using the blood pressure measuring device according to an embodiment of the present disclosure.

Figure 18:
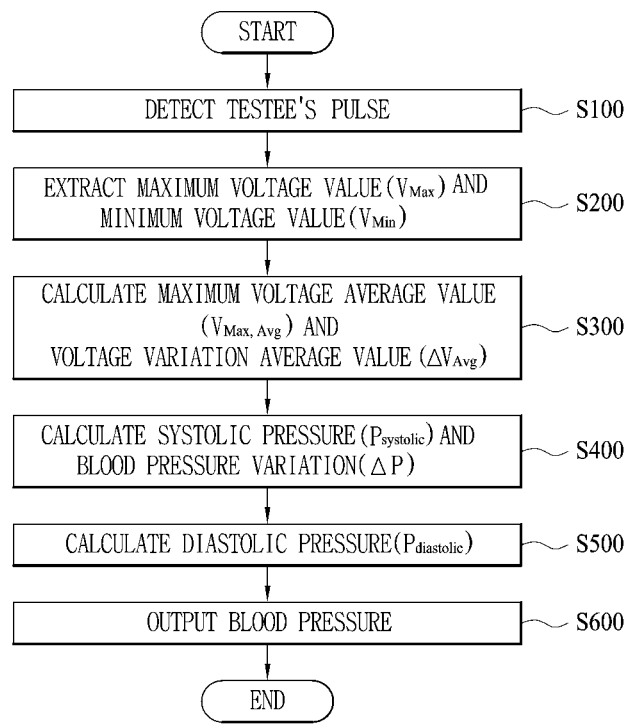
FIG. 18 is a flowchart illustrating a method of measuring blood pressure using the blood pressure measuring device according to an embodiment of the present disclosure.

Referring to FIG. 18, the method of measuring blood pressure by the blood pressure measuring device according to an embodiment of the present disclosure may include a first operation S100 of allowing the pulse sensing module 110 to detect a pulse signal for a predetermined time and generate a voltage signal due to a piezoelectric effect when the testee wears the blood pressure measuring device 100 on the wrist and requests blood pressure measurement therefrom, a second operation S200 of extracting the maximum voltage value $V_{Max}$ and the minimum voltage value $V_{Min}$ of the voltage signal that corresponds to each pulse signal for the predetermined time, a third operation S300 of calculating the maximum voltage average value $V_{Max,Avg}$, which is an average value for the maximum voltage value $V_{Max}$ extracted from the voltage signal for each pulse signal and calculating a voltage variation average value $\Delta V_{Avg}$, which is an average value for the difference between the maximum voltage value $V_{Max}$ and the minimum voltage value $V_{Min}$ extracted from the voltage signal for each pulse signal, a fourth operation S400 of calculating the systolic pressure $P_{systolic}$ and the blood pressure variation $\Delta P$ from the maximum voltage average value $V_{Max,Avg}$ and the voltage variation average value $\Delta V_{Avg}$, respectively, on the basis of the relationship based on big data analysis, a fifth operation S500 of calculating the diastolic pressure $P_{diastolic}$ by subtracting the blood pressure variation $\Delta P$ from the systolic pressure $P_{systolic}$, and a sixth operation S600 of outputting a calculated result value.

In this case, the second to fifth operations S200 to S500 may be performed by the control unit 126 of the blood pressure calculation module 120, and the sixth operation S600 may be performed by the display module or the external device.

Prior to the second operation S200, operations of amplifying and filtering a voltage signal due to a piezoelectric effect provided through the pulse sensing module 110 and then converting the voltage signal to a digital signal may be performed.

A pulse sensing module, a blood pressure calculation module, a blood pressure measuring device, and a method of manufacturing a pulse sensing module according to the present disclosure enable blood pressure to be measured through a piezoelectric effect of a piezoelectric material on pulse, thereby providing convenience to a testee.

Further, the relationship between a voltage signal caused by the piezoelectric effect and blood pressure can be clearly defined, thereby improving accuracy of blood pressure measurement.

Further, the blood pressure measuring device according to the present disclosure can be manufactured as a patch or band type device to be made compact while enabling accurate blood pressure to be measured regardless of the curved skin characteristics of the human body and human activity, thereby significantly increasing utilization.

Meanwhile, each operation of the above-mentioned blood pressure measurement method can be implemented as a computer-readable code that is stored on a computer-readable recording medium. The computer-readable recording medium includes all kinds of recording devices in which data readable by a computer system is stored. Examples of the computer-readable recording medium include a read only memory (ROM), a random access memory (RAM), a compact disc read-only memory (CD-ROM), a magnetic tape, a floppy disk, and an optical data storage, and also include recording media that are implemented in the form of a carrier wave (for example, transmission over the Internet). Further, the computer-readable recording medium may be distributed over a networked computer system so that a computer-readable code can be stored and executed in a distributed manner.

While the configurations and features of the present disclosure have been described with reference to the embodiments according to the present disclosure, the present disclosure is not limited thereto. It will be apparent to those skilled in the art that various changes or modifications may be made within the spirit and scope of the present disclosure as defined by the appended claims.

What is claimed is:

1. A blood pressure measuring device configured for being attached to the skin during use for measurement of at least one of systolic pressure, diastolic pressure, and blood pressure variation, the blood pressure measuring device comprising:
   a pulse sensing module;
   a blood pressure calculation module that is configured to calculate the at least one of the systolic pressure, the diastolic pressure, and the blood pressure variation using a voltage signal generated by the piezoelectric effect, wherein the blood pressure calculation module is configured to extract a maximum voltage value $V_{Max}$ and a minimum voltage value $V_{Min}$ of the voltage signal that is obtained by the pulse sensing module and corresponds to each pulse signal for a predetermined time and then to calculate the at least one of the systolic pressure, the diastolic pressure, and the blood pressure variation on the basis of the extracted maximum voltage value $V_{Max}$ and minimum voltage value $V_{Min}$; and
   the blood pressure calculation module is configured to calculate a maximum voltage average value $V_{Max,Avg}$, which is an average value for the maximum voltage value $V_{Max}$ extracted from the voltage signal for each pulse signal and to calculate a voltage variation average value $\Delta V_{Avg}$, which is an average value for the difference between the maximum voltage value $V_{Max}$ and the minimum voltage value $V_{Min}$ extracted from the voltage signal for each pulse signal to calculate the at least one of the systolic pressure, the diastolic pressure, and the blood pressure variation.

2. The blood pressure measuring device of claim 1, wherein the blood pressure calculation module is configured to calculate, on the basis of a relationship based on a data analysis, the systolic pressure and the blood pressure variation $\Delta P$ from each of the maximum voltage average value $V_{Max,Avg}$ and the voltage variation average value $\Delta V_{Avg}$.

3. The blood pressure measuring device of claim 2, wherein a relationship between the maximum voltage average value $V_{Max,Avg}$ and the systolic pressure $P_{systolic}$ on the basis of the data analysis satisfies the following Conditional Expression 1:

$$P_{systolic} = \frac{V_{Max,Avg} - \beta}{\alpha}, \qquad \text{<Conditional Expression 1>}$$

where $P_{systolic}$ is systolic pressure, $V_{Max,Avg}$ is a maximum voltage average value, and $\alpha$ and $\beta$ are constants that are derived by using data analysis.

4. The blood pressure measuring device of claim 3, wherein a relationship between the voltage variation average value $\Delta V_{Avg}$ and the blood pressure variation $\Delta P$ on the basis of the data analysis satisfies the following Conditional Expression 2:

$$\Delta P = -\gamma \times \Delta V_{Avg} + \delta, \qquad \text{<Conditional Expression 2>}$$

where ΔP is blood pressure variation, $\Delta V_{Avg}$ is a voltage variation average value, and γ and δ are constants that are derived by using data analysis.

5. The blood pressure measuring device of claim 4, wherein the blood pressure calculation module is configured to subtract the blood pressure variation ΔP from the systolic pressure $P_{systolic}$ to calculate the diastolic pressure $P_{diastolic}$.

6. The blood pressure measuring device of claim 1, wherein the blood pressure calculation module includes:
 a signal preprocessing unit that is configured to amplify an amplitude of the voltage signal generated by the piezoelectric effect and filters noise;
 a conversion unit that is configured to convert, to a digital signal, the voltage signal pre-processed by the signal preprocessing unit and to output the digital signal; and
 a control unit that is configured to calculate the at least one of the systolic pressure, the diastolic pressure, and the blood pressure variation on the basis of the voltage signal converted by the conversion unit.

7. The blood pressure measuring device of claim 1, further comprising a bending module that has the pulse sensing module and the blood pressure calculation module attached thereto and is bendable to allow the blood pressure measuring device to be tightly attached to a curved skin surface of the human body.

8. A blood pressure measuring device configured for being attached to the skin during use for measurement of at least one of systolic pressure, diastolic pressure, and blood pressure variation, the blood pressure measuring device comprising:
 a pulse sensing module comprising:
  a piezoelectric layer that includes a piezoelectric material for generating a piezoelectric effect due to a pulse, wherein a first electrode line and a second electrode line disposed to be spaced apart from each other are formed on one surface of the piezoelectric layer; and
  a protective layer that is applied to the one surface of the piezoelectric layer and over the first electrode line and second electrode line to protect the piezoelectric layer, allows a poling process of applying a voltage to the first electrode line and the second electrode line to improve the polarity of the piezoelectric material, and has an opening for allowing a portion of the first electrode line and a portion of the second electrode line to be exposed such that the first electrode line and the second electrode line are electrically connected to a blood pressure calculation module of the blood pressure measuring device, wherein the blood pressure calculation module is configured to calculate the at least one of the systolic pressure, the diastolic pressure, and the blood pressure variation using a voltage signal generated by the piezoelectric effect; and
 a blood pressure calculation module that is configured to calculate the at least one of the systolic pressure, the diastolic pressure, and the blood pressure variation using a voltage signal generated by the piezoelectric effect,
 wherein the blood pressure calculation module is configured to extract a maximum voltage value $V_{Max}$ and a minimum voltage value $V_{Min}$ of the voltage signal that is obtained by the pulse sensing module and corresponds to each pulse signal for a predetermined time and then to calculate the at least one of the systolic pressure, the diastolic pressure, and the blood pressure variation on the basis of the extracted maximum voltage value $V_{Max}$ and minimum voltage value $V_{Min}$,
 wherein the blood pressure calculation module is configured to calculate a maximum voltage average value $V_{Max,Avg}$, which is an average value for the maximum voltage value $V_{Max}$ extracted from the voltage signal for each pulse signal and to calculate a voltage variation average value $\Delta V_{Avg}$, which is an average value for the difference between the maximum voltage value $V_{Max}$ and the minimum voltage value $V_{Min}$ extracted from the voltage signal for each pulse signal to calculate the at least one of the systolic pressure, the diastolic pressure, and the blood pressure variation.

9. The blood pressure measuring device of claim 8, wherein the blood pressure calculation module is configured to calculate, on the basis of a relationship based on a data analysis, the systolic pressure and the blood pressure variation ΔP from each of the maximum voltage average value $V_{Max,Avg}$ and the voltage variation average value $\Delta V_{Avg}$.

10. The blood pressure measuring device of claim 9, wherein a relationship between the maximum voltage average value $V_{Max,Avg}$ and the systolic pressure $P_{systolic}$ on the basis of the data analysis satisfies the following Conditional Expression 1:

$$P_{systolic} = \frac{V_{Max,Avg} - \beta}{\alpha}, \quad \langle\text{Conditional Expression 1}\rangle$$

where $P_{systolic}$ is systolic pressure, $V_{Max,Avg}$ is a maximum voltage average value, and α and β are constants that are derived by using data analysis.

11. The blood pressure measuring device of claim 10, wherein a relationship between the voltage variation average value $\Delta V_{Avg}$ and the blood pressure variation ΔP on the basis of the data analysis satisfies the following Conditional Expression 2:

$$\Delta P = -\gamma \times \Delta V_{Avg} + \delta, \quad \langle\text{Conditional Expression}\rangle$$

where ΔP is blood pressure variation, $\Delta V_{Avg}$ is a voltage variation average value, and γ and δ are constants that are derived by using data analysis.

12. The blood pressure measuring device of claim 11, wherein the blood pressure calculation module is configured to subtract the blood pressure variation ΔP from the systolic pressure $P_{systolic}$ to calculate the diastolic pressure $P_{diastolic}$.

* * * * *